United States Patent [19]

Brennan et al.

[11] Patent Number: 4,873,461
[45] Date of Patent: Oct. 10, 1989

[54] ELECTRIC MOTOR STERILIZABLE SURGICAL POWER TOOL

[75] Inventors: Thomas J. Brennan, Kalamazoo; James A. Evans, Galesburg, both of Mich.

[73] Assignee: Stryker Corporation, Kalamazoo, Mich.

[21] Appl. No.: 193,882

[22] Filed: May 13, 1988

[51] Int. Cl.[4] .................. H02K 1/18; H02K 5/04; H02K 21/28
[52] U.S. Cl. ............................ 310/47; 310/154
[58] Field of Search ........... 310/40 MM, 47, 50, 154, 310/254, 266, 89; 29/596

[56] References Cited

U.S. PATENT DOCUMENTS

| 3,494,799 | 2/1970 | Pedone, Jr. | 310/47 |
| 4,237,393 | 12/1980 | Landgraf | 310/47 |
| 4,453,097 | 6/1984 | Lordo | 310/154 |
| 4,661,729 | 4/1987 | Hames et al. | 310/154 |
| 4,682,066 | 7/1987 | Abbratozzato et al. | 310/50 |
| 4,707,630 | 11/1987 | Tomite et al. | 310/154 |
| 4,745,319 | 5/1988 | Tomite et al. | 310/154 |
| 4,795,932 | 1/1989 | Long | 310/154 |

FOREIGN PATENT DOCUMENTS

| 168743 | 1/1986 | European Pat. Off. | 310/254 |
| 57-16561 | 1/1982 | Japan . | |
| 58-54861 | 3/1983 | Japan . | |
| 59-6759 | 2/1984 | Japan . | |
| 123933 | 6/1987 | Japan | 310/254 |

Primary Examiner—Patrick R. Salce
Assistant Examiner—D. L. Rebsch
Attorney, Agent, or Firm—Flynn, Thiel, Boutell & Tanis

[57] ABSTRACT

An electric motor suitable for use in a steam sterilizable surgical tool comprising a casing with a peripheral wall, plural magnets, an armature and structure rotatably supporting them in the casing, structure locating the magnets axially and circumferentially in the casing, and a sleeve radially outwardly pressing against the magnets. Wedged rings can supply part or all of the outward pressure on the sleeve.

16 Claims, 2 Drawing Sheets

ELECTRIC MOTOR STERILIZABLE SURGICAL POWER TOOL

FIELD OF THE INVENTION

This invention relates to an electric motor and more particularly to an electric motor which is sterilizable under conditions of high temperature and moisture, as in sterilization of a surgical tool.

BACKGROUND OF THE INVENTION

Surgical hand tools of electrically powered type have long been known. Reusable tools of this type must be sterilized prior to surgical use on each new patient. Particularly effective sterilization can be obtained by exposing the hand tool to high temperature steam for a period of time.

However, in electrically powered tools of this type, the repeated application of high temperature and humidity, due to recurring placement in a steam autoclave or the like, has damaged electrical motors of the type having a rotating armature surrounded by permanent magnets adhesively bonded to the interior surface of the surrounding motor casing. The adhesive bonding is typically done by an epoxy or related resin. At room temperature and moderate humidity levels, such bond strongly and reliably holds the magnets in place within the casing. However, it has been found that the high temperature and humidity environment encountered in sterilizing the tool tends to degrade such adhesive bond, such that magnets have become loose within their casings and have rendered their respective motors inoperative, thereby rendering the corresponding surgical tool inoperative.

Further in permanent magnet motors of this kind, even if not to be subjected to high moisture and temperature conditions, permanent affixing of the magnets in the casing by adhesive bonding has the further disadvantages of being time consuming, relatively expensive, subject to error in location and being subject to unreliability if bonding conditions are not precisely controlled (e.g. if surfaces are not clean, temperature is out of range, etc.).

Accordingly, the objects and purposes of this invention include provision of apparatus directed to overcoming the aforementioned problems in prior art devices.

SUMMARY OF THE INVENTION

The objects and purposes of the invention are met by providing an electric motor suitable for use in a steam sterilizable surgical tool, such electric motor comprising a casing with a peripheral wall, a plurality of magnets, an armature and means rotatably supporting same in said casing, means locating said magnets axially and circumferentially in said casing, and means radially outwardly pressing against said magnets to fix same radially in said casing, said means comprising a sleeve axially insertable in said casing and radially interposed between said magnets and armature.

Further objects of the invention will be apparent to persons acquainted with apparatus of this general type upon reading the following specification and inspecting the accompanying drawings.

DETAILED DESCRIPTION

Figure 1:
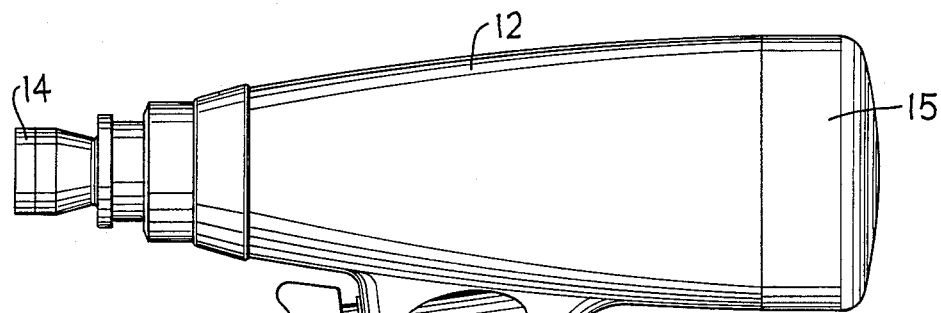
FIG. 1 is a partially broken view of a sterilizable surgical tool embodying the invention.
Figure 1A:
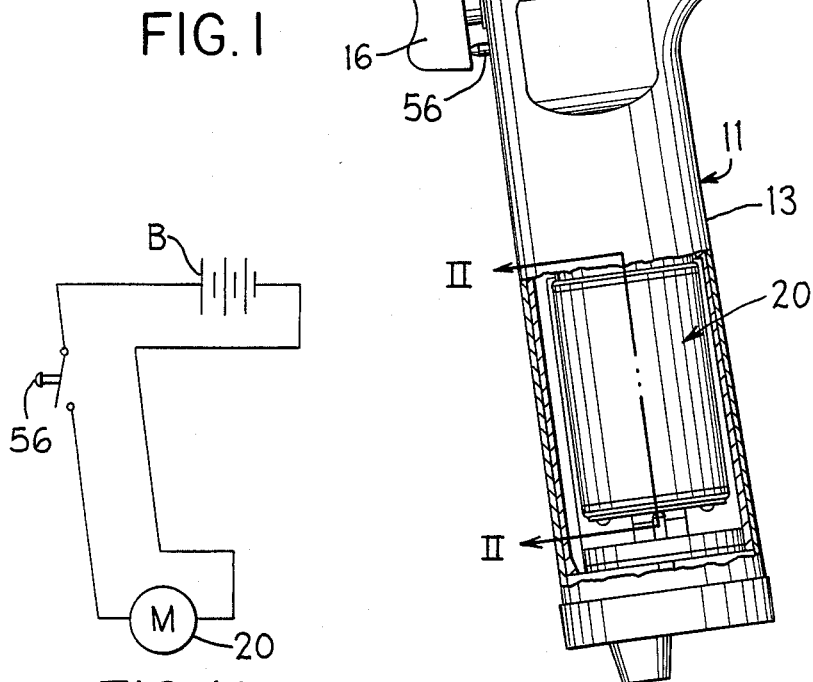
FIG. 1A is a wiring schematic of the FIG. 1 tool.

A rotary surgical tool 10 (FIG. 1) comprises a pistol shaped housing 11 comprising a barrel-shaped body 12 (horizontally oriented in FIG. 1) from which depends a handgrip 13. Protruding leftwardly from the corresponding end of the barrel 12 is a rotatable chuck 14 adapted to receive a rotatable tool (cutter, grinder or the like) not shown. In the embodiment shown, the opposite end (right in FIG. 1) of the barrel is closed by a cap 15 which is removable for replacement of a battery B. A trigger 16 high on the front (left in FIG. 1) side of the grip 13 is pressable by the human operator to apply electric current from the battery B in compartment 15 to an electric motor 20 fixedly located within the lower portion of the butt 13. The motor 20 has an output shaft 21 (FIG. 2) connected by a power train, including a shaft supported gear 22, for rotating the chuck 14 in response to electrical actuation of the motor 20.

The motor 20 further comprises a casing 23 having a circular cross-section peripheral wall 24 closed at its axial ends by end members 25 and 26. The shaft 21 is rotatably supported on bearings 30 and 31 centrally fixed in recesses in the end walls 25 and 26 of the casing 23. The shaft 21 protrudes leftwardly (FIG. 2) through a central opening 32 in the left casing in wall 25. An armature 33 is coaxially fixed on the shaft 21 for rotation therewith and here is provided with reduced diameter, progressively stepped down portions 34, 35 and 36 at the rightward end thereof. The reduced diameter portion 36 is provided with brush engaging electrical contacts 37. The armature 33 also includes a reduced diameter leftward portion 41. DC electric current is supplied to conductive windings (not shown) in the maximum diameter portion 42 of the armature 33 by means of brushes 43 and 44 which bear on the rotating brush contact 37 of the armature 33.

Figure 4:
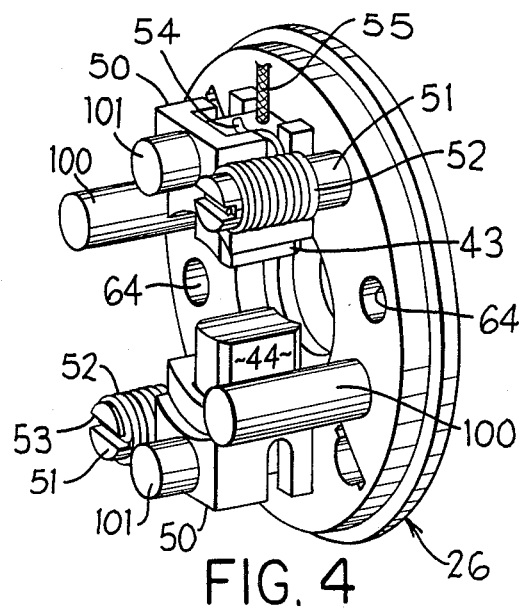
FIG. 4 is a pictorial view of the rightward end member of the FIG. 2.

The brushes 43 and 44 are diametrically opposed on opposite sides of the armature portion 36 and are diametrically slidable in rectangular cross-section guideways 50 defined by hollow bosses protruding axially inward from the rightward casing end member 26. Diametrically opposed, pin-like, coil spring supports 51 (FIG. 4) fixedly protrude axially inboard from the rightward casing end member 26. The supports 51 are located circumferentially beside corresponding ones of the guideways 50. A coil spring 52 is wound on each support 51. Each spring 52 has one end stepped in a diametral slot 53 in the inboard end of the corresponding support 51. The remaining end 54 of each spring 52 extends from the corresponding support 51 to back the radially outward end of the corresponding brush 43 or 44 to resiliently urge such brush radially inward toward the armature portion 36 on which it bears. Each brush 43 receives electric current from an electric conductor 55 embedded in the radially outward end thereof and connected through an electric switch 56 contained in the grip 13 to the battery (not shown) held in the barrel 12 by the cap 15.

Figure 2:
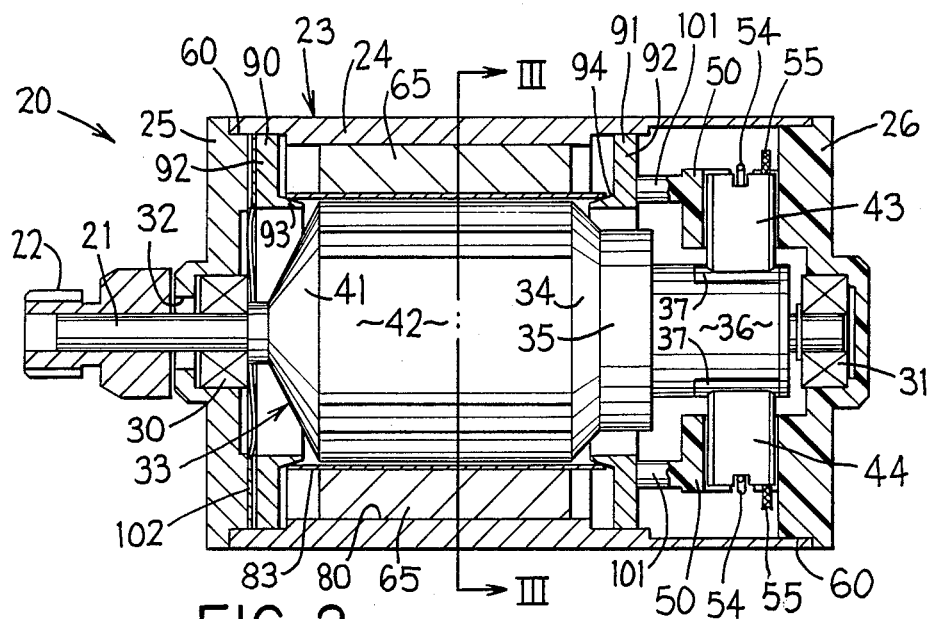
FIG. 2 is a central cross-sectional view, substantially has taken along the line II—II of FIG. 1 and disclosing an electric motor embodying the invention.
Figure 3:
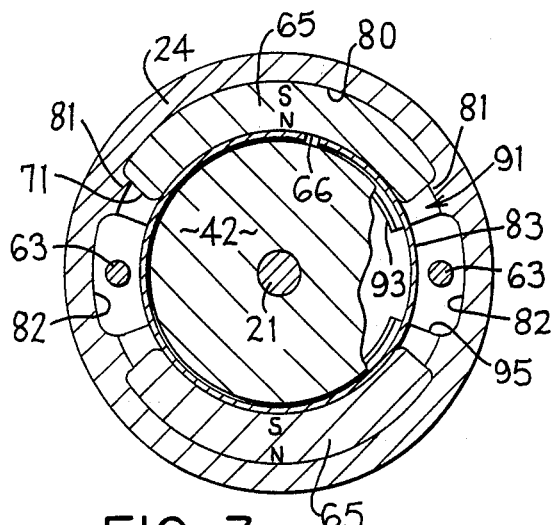
FIG. 3 is a partially broken cross-sectional view substantially taken on the line III—III of FIG. 2.

The end members 25 and 26 are stepped at their periphery is indicated at 60 (FIGS. 2 and 4) to axially engage and fit snugly radially within the ends of the peripheral casing wall 24. The end members 25 and 26 are held rigidly fixed against the ends of the casing peripheral 24 by elongate screws 63 (FIG. 3). In the embodiment shown, a pair of screws 63 are provided and are located radially just inboard of the casing peripheral wall 24. The screws 63 extend through corresponding holes 64 on the rightward end member 26 (FIG. 4) and threadedly engage correspondingly located holes (not shown) in the left end member 25. Tightening of the screws 63 thus pulls the end members 25, 26 tightly against the ends of the peripheral 24.

Plural permanent magnets 65 (FIGS. 2 and 3) are fixed to the interior surface of the casing peripheral 24 and are circumferentially spaced therealong. In the embodiment shown, the plurality of magnets comprises two semicircular magnets which are diametrically opposed to each other. Less desirably, each magnet 65 could be substituted by several circumferentially narrower magnets. The radially interior surfaces 66 of the magnets 65 are spaced radially by a narrow annular magnetic gap from the peripheral surface of the maximum diameter portion 42 of the armature 43. The screws 63 are circumferentially spaced between the circumferential ends 71 of adjacent magnets 65.

To the extent above-described, the foregoing apparatus is conventional.

Turning now to aspects of the disclosed apparatus more directly concerning the present invention, attention is directed to means for rigidly locating the permanent magnets 65 in fixed location within the casing 24. Circumferentially extending, axially open ended grooves 80 (FIG. 3) are formed (for example by a milling operation) in the interior surface of the casing peripheral wall 24. The grooves 80 compliment the shape of the radially outer portion of the magnets 65 so that the magnets 65 fit snugly within the corresponding grooves 80. The radial depth of the grooves 80 is less than the radial thickness of the magnets 65, such that the magnets 65 protrude radially inward from the grooves 80. The inner surface of the casing 24 has radially inward protruding, axially extending abutments 81 (FIG. 3) defining the circumferential ends of the grooves 80 and abutting the circumferential ends of the magnets 65 to locate same in fixed circumferential location within the casing peripheral wall 24.

To accommodate the diametrically opposed screws 63, the interior surface of the casing peripheral wall 24 is provided with further, axially open, relatively circumferentially narrow grooves 82. The screws 63 extend loosely through the grooves 82. The screw accommodation grooves 82 are circumferentially separated from the magnet receiving grooves 80 by corresponding ones of the abutments 81.

As hereafter discussed in connection with assembly of the motor, the magnets 65 are axially located within the casing peripheral wall 24 by means of a suitable fixture (not shown) and are fixed in place within the casing by suitable temporary means such as a suitable adhesive. The adhesive need not be resistent to high temperatures or humidity since it is merely a temporary means of location.

A sleeve, in the preferred embodiment shown, a single longitudinally split sleeve 83 (FIGS. 2 and 3), is received radially between the magnets 65 and maximum diameter portion 42 of the armature 33. The sleeve is of relatively thin material, in the preferred embodiment shown about 0.015 inch thick, to permit retention of a radially narrow magnetic gap between the armature portion 42 and magnets 65, for maximum efficiency of the motor. Despite its thinness, the split sleeve 83 is of stiff material, so as to retain its shape in the annular magnetic gap between the armature portion 42 and magnets 65.

Figure 6:
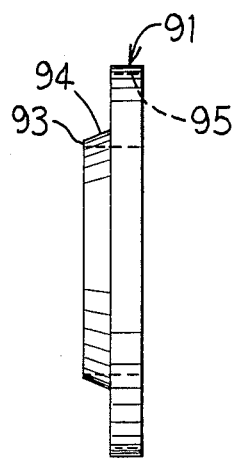
FIG. 6 is a side view of the FIG. 5 annular wedge.
Figure 7:
FIG. 7 is a side view of a suitable wave washer.

Annular wedges 90 and 91 are provided at opposite ends of the sleeve 83 for radially expanding the sleeve slightly, sufficiently to press it radially outward against the inner surfaces of the magnets 65, and to keep it out of contact with the peripheral surface of the maximum diameter portion 42 of the armature 33. The annular wedges 90 and 91 are preferably identical to each other and, when installed in the motor, as seen in FIG. 2, are in opposed, mirror imaged relation. The wedges 90 and 91 each comprise a flat annular member 92, from the inner periphery of which axially protrudes an axial flange 93. The radially outer surface 94 (FIG. 6) of the axial flange is tapered toward the free end of such flange. As seen in FIG. 2, the annular wedges 90 and 91 are arranged within the casing 23 with the axial flanges thereof pointing toward each other and received in the ends of the split sleeve 83, so that the tapered, radially outward surfaces 94 of the axial flanges 93 are received in the ends of the split sleeve 83. The annular wedges 90 and 91 are provided with radially inwardly opening, circumferentially extending recesses 95, which are diametrically opposed and are arranged to loosely accommodate the screws 63.

To press the annular wedges 90 and 91 axially against the split sleeve 83, to in turn radially expand the split sleeve firmly radially outward against the magnets 65, means associated with the end members 25 and 26 engages the axially outer surfaces of the flat annular members 92 of the annular wedges 90 and 91. More particularly, the rightward end member 26 is provided with axially inwardly extending, circumferentially distributed posts 100 and 101. One diametrically opposed pair of posts 100 is circumferentially spaced between the poles 64 and guideways 50. The other diametrically opposed pair of posts 101 extends axially from and is fixed with respect to the respective guideways 50. The axially inward ends of the posts 100 and 101 are in a common radial plane and, as seen in FIG. 2, in the assembled motor, bear against the outer axial faces of the rightward annular wedge 91.

Figure 5:
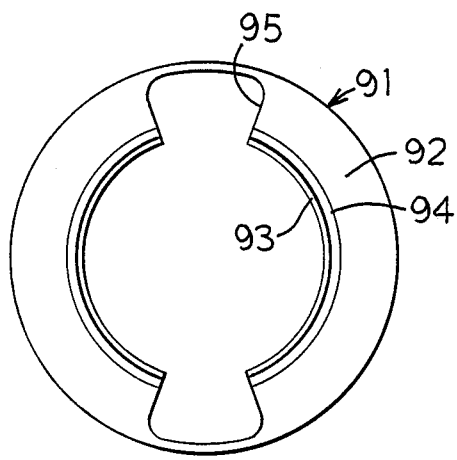
FIG. 5 is an annular wedge of the FIG. 2 motor, as seen looking from the same direction as in FIG. 3.

A conventional wave washer 102 (FIG. 5) of suitable springy metal material is axially disposed between and axially urges apart the leftward annular wedge 90 and leftward casing end member 25. Thus, with the rightward annular wedge 91 fixed against rightward movement by the posts 100 and 101, the wave washer 102 axially forces the annular wedge 90 rightwardly toward the rightward annular wedge 91, such that the tapered surfaces 94 thereof are urged axially inwardly of the split sleeve 83 and thereby expand the split sleeve radially outwardly against the magnets 65 to fixedly secure the magnets within the casing. Thus, the magnets 65 remain fixed within the casing even when the motor and tool are repetitively subjected to high temperature and moisture conditions during repeated sterilizing operations over the life of the tool, independent of any adhesive bond between the magnets 65 and the inner surface of the casing peripheral wall 24. Indeed, if a temporary adhesive is utilized during assembly to temporarily fix the magnets 65 to the interior surface of the peripheral wall 24 of the casing, it is contemplated that such adhesive may of the type which will fail after the motor 20 is assembled, perhaps even before the first sterilization of it.

In one unit constructed according to the invention, the magnets 65 were of samarium cobalt, which magnets are advantageously corrosion resistent and have high magnetic field intensity for their physical size. The casing peripheral wall 24 was of low carbon steel, advantageous because of its high magnetic permeability, the casing being electroless nickel plated inside and outside for corrosion resistance. The split sleeve 83 was of stainless steel, magnetically inert and having a Rockwell C rating in the low 30's. The split sleeve may for example be of no. 302 or 304 stainless steel which is relatively stiff and springy. The screws 63 were of stainless steel. The end cap 25 was of black anodized aluminum. The end cap 26 (including the brush supports) was of a black multiple plastic material. For corrosion resistance, the armature, in the region of the windings and lamentations in the area 41, 42, 35, 36 was coated with a high temperature varnish for corrosion protection, the brushes making electrical contact with the portions 37 of the armature. Again for corrosion resistance, the springs 52 (FIG. 4), and the annular wedges 90 and 91, and the wave washer 102 were of stainless steel.

While different methods are contemplated, the motor structure can be assembled as follows. With the magnets 65 not yet magnetized, a temporary adhesive may be applied to the outer diameter of such magnets. The magnets 65 are thereafter axially guided into the axial grooves 80 in the inner periphery of the peripheral wall 24 of the casing. A fixture, not shown, inserted in the far end of the casing peripheral wall, stops the axial advance of the magnets at the desired position shown in FIG. 2. After the temporary adhesive sets, the fixture is withdrawn and the magnets 65 are thus temporarily held fixed within the casing peripheral wall 24. The internal diameter of the magnets 65 can then be ground to the precise desired internal diameter. Thereafter, the magnets 65 can be magnetized with the polarity indicated in FIG. 3 so that the north (N) pole of one magnet 65 is at the radially inner face thereof and the south (S) pole of the other magnet 65 is at the radially inner surface thereof.

Thereafter, the split sleeve 83, annular wedges 90 and 91, the wave washer 102, and the end caps 25 and 26 can be axially inserted to their positions shown in FIG. 2 and then held in place by installation of the screws 63. The screws 63, thus installed, hold the end caps 25 and 26 firmly axially against the ends of the casing peripheral 24, and thereby cause the posts 100 and 101 on the end cap 26 to locate the annular wedge 91 axially against the split sleeve 83, so that the wave washer 102, backed by the end cap 25, resistantly pushes toward each other the annular wedges 90 and 91 to expand the split sleeve 83 radially outward against the magnets 65. The thus expanded split sleeve 83 thus firmly presses the magnets 65 radially outward against the casing wall and frictionally holds same fixedly in position within the casing, despite subjecting the motor and the tool 10 to adverse environments, for example, repeated sterilizing with high temperature steam (high temperature and high moisture conditions). The temporary adhesive, which is convenient to use to hold the magnets 65 temporarily fixed within the casing peripheral wall 24 during assembly, is thus no long needed after assembly. The tendency of such adhesive to thereafter degrade and become ineffective is thus immaterial, since it is the annular wedges 90 and 91 and the split sleeve 83 which fix the magnets 65 permanently into position within the casing peripheral wall 24.

While the motor 20 embodying the invention is disclosed above in connection with a surgical hand tool, it is contemplated that motors embodying the invention are capable of a variety of other uses.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An electric motor comprising:
   a casing having a peripheral wall;
   circumferentially distributed magnets lining the inside of the peripheral wall of the casing;
   means on said casing locating said magnets axially and circumferentially with respect to said casing;
   an armature and means on said casing rotatably supporting said armature within said casing;
   a split sleeve radially interposed between said magnets and said armature;
   means bearing on the ends of said split sleeve for expanding said split sleeve radially away from said armature and firmly radially outwardly pressing said sleeve against said magnets and thereby for holding said magnets fixedly against the inner periphery of said casing; and
   whereby said magnets are held in place in said casing without need for adhesive bonding to said casing.

2. The device of claim 1 in which said sleeve is split longitudinally so as to extend circumferentially less than 360°, said sleeve being radially thin compared to said magnets, said sleeve being of nonmagnetic material, said sleeve being rigid but resiliently radially expandable 3. An electric motor comprising:
   a casing having a peripheral wall;
   circumferentially distributed magnets lining the inside of the peripheral wall of the casing;
   means on said casing locating said magnets axially and circumferentially with respect to said casing;
   an armature and means on said casing rotatably supporting said armature within said casing;
   a split sleeve radially interposed between said magnets and said armature;
   means bearing on the ends of said split sleeve for expanding said split sleeve radially away from said armature and into firm radially outward pressure against said magnets and thereby for holding said magnets fixedly against the inner peripheral wall of said casing; and
   whereby said magnets are held in place in said casing without need for adhesive bonding to said casing, said means radially outwardly pressing comprising first and second annular wedges received within the opposite ends of said split sleeve and means in said casing for pressing axially against the ends of said split sleeve and thereby radially outwardly pressing said sleeve against the magnets to fix said magnets in said casing.

4. The device of claim 3 in which said annular wedges each comprise a flat annular member from which protrudes an axial flange, the radially outer surface of said axial flange being tapered toward the free end of said axial flange, said tapered outer surface of said flange being snugly insertable axially into the adjacent end of said sleeve, such that pressing of said flat annular members axially toward each other wedges said sleeve radially outward against said magnets.

5. The apparatus of claim 4 in which said armature has an outer peripheral surface radially opposing said sleeve, the axial ends of said split sleeve extending beyond said outer peripheral surface of said armature, said tapered axial flanges of said flat annular members being receivable radially between end potions of said split sleeve and portions of said armature axially protruding beyond said outer peripheral surface and being of diameter smaller than said outer peripheral surface.

6. The device of claim 3 in which said means for pressing axially comprise end members closing the ends of said casing and resilient means interposed between at least one of said end members and a corresponding annular wedge for pressing said wedges against the ends of said sleeve and thereby radially expanding the sleeve outward against the magnets.

7. The device of claim 6 in which said resilient means comprises a wave washer.

8. The device of claim 6 including elongate screws extending through said casing between said end members to permit removal of at least one said end cap and to axially press said end members against said casing, eccentric openings in said wedges for receiving said screws loosely therethrough, and backing means adjacent at least one of said end members for pushing the adjacent annular wedge axially against said split sleeve.

9. The device of claim 8 in which said backing means comprises plural, eccentrically located, axially extending studs extending axially inward from said one end member, said studs having free ends located in a common radial plane for abutting the adjacent wedge.

10. An electric motor comprising:
a casing having a peripheral wall;
an armature rotatable within said casing and means rotatably supporting said armature with respect to said casing;
a plurality of magnets distributed circumferentially within said casing radially outboard of said armature;
plural axially extending abutments protruding integrally and radially inward from the inner surface of said casing peripheral wall, said abutments being circumferentially spaced to define axially extending slots opening radially toward said armature and of circumferential extent to snugly receive therebetween respective ones of said magnets, said slots opening axially of said casing for sliding said magnets axially therein during assembly of the motor, said abutments having circumferentially facing sidewalls and said magnets having circumferentially facing edgewalls of complementary shape so that the magnets snugly abut in substantial surface contact with said abutments; and
means for radially outwardly urging said magnets against the casing peripheral wall so as to maintain same out of contact with said armature.

11. The device of claim 10 in which the circumferential ends of said slots and of said magnets are substantially radial, said magnets protruding radially inward from said slots toward said armature, said means radially outwardly urging locating said magnets in said casing comprising a sleeve received radially between said armature and magnets, said sleeve radially outwardly pressing forcibly against said maganets.

12. An electric motor comprising:
a casing having a peripheral wall;
an armature rotatable within said casing and means rotatably supporting said armature with respect to said casing;
a plurality of magnets distributed circumferentially within said casing radially outboard of said armature;
plural axially extending abutments fixed to the inner surface of said casing peripheral wall, said abutments being circumferentially spaced to define axially extending slots opening radially toward said armature and of circumferential extent to snugly receive therebetween respective ones of said magnets, said abutments having circumferentially facing sidewalls and said magnets having circumferentially facing edgewalls of complementary shape so that the magnets snugly abut in substantial surface contact with said abutments; and
means for radially securing said magnets in place in said casing so as to maintain same out of contact with said armature, said means radially locating said magnets in said casing comprising a sleeve received radially between said armature and magnets, said sleeve radially outwardly pressing forcibly against said magnets, said sleeve being an axially split sleeve, means radially outwardly expanding said sleeve against said magnets, said means comprising annular wedges received within the opposite ends of said split sleeve and means in said casing for pressing said wedges axially in against the ends of split sleeve and thereby radially outwardly pressing said sleeve against said magnets to fix same in said casing.

13. An electrically powered surgical hand tool, comprising:
a pistol shaped housing of the type having a barrel terminating in a rotatable chuck and a depending handgrip;
a trigger control on said handgrip and an electric motor housed within said handgrip for powering said chuck in response to actuation of said trigger, said motor being sterilizable by subjecting same to high temperature steam, said motor having a casing, an armature rotatable within said casing, plural permanent magnets circumferentially distributed within said casing in loosely surrounding relation to said armature, said armature being rotatable with respect to said magnets, a split sleeve loosely surrounding said armature and held tightly radially outwardly against said magnets to fix same within said casing by means including wedges at opposite ends of said split sleeve and means in said casing for pressing said wedges axially toward each other to wedge radially outward the ends of said sleeve and thereby to press said sleeve radially outwardly against said magnets and fix same with respect to said casing.

14. An electric motor comprising:
a casing having a peripheral wall;
circumferentially distributed magnets lining the inside of the peripheral wall of the casing;
means on said casing locating said magnets axially and circumferentially with respect to said casing;
an armature and means on said casing rotatably supporting said armature within said casing;
means radially outwardly pressing against said magnets to fix same radially in said casing, said means comprising a sleeve axially insertable in said casing and radially interposed between said magnets and armature, said sleeve being axially split, said radially outward pressing means further including means actuable for radially outwardly expanding said split sleeve forcibly against said magnets.

15. The device of claim 14 in which said sleeve radially clears said armature so as not to interfere with rotation of said armature, said sleeve being sufficiently thin as to radially fit in the radial magnetic gap between the magnets and armature, said sleeve being of relatively stiff, nonmagnetic material.

16. The device of claim 15 in which said sleeve is of stainless steel of about 0.010 to 0.020 inch thickness.

* * * * *

UNITED STATES PATENT AND TRADEMARK OFFICE
CERTIFICATE OF CORRECTION

PATENT NO. : 4,873,461
DATED : October 10, 1989
INVENTOR(S) : Thomas J. Brennan et al It is certified that error appears in the above-identified patent and that said Letters Patent is hereby corrected as shown below:

Column 7, line 20, "potions" should read --portions--.

Signed and Sealed this

Fourth Day of December, 1990

Attest:

HARRY F. MANBECK, JR.

*Attesting Officer*   *Commissioner of Patents and Trademarks*

UNITED STATES PATENT AND TRADEMARK OFFICE
CERTIFICATE OF CORRECTION

PATENT NO. : 4,873,461

DATED : October 10, 1989

INVENTOR(S) : Thomas J. Brennan et al

It is certified that error appears in the above-identified patent and that said Letters Patent is hereby corrected as shown below:

Col. 8, line 8; delete "locating".

Col. 8, line 11, "maganets" should read --magnets--

Signed and Sealed this

Fourth Day of June, 1991

Attest:

HARRY F. MANBECK, JR.

*Attesting Officer*  *Commissioner of Patents and Trademarks*